United States Patent
Young

(10) Patent No.: US 6,656,969 B2
(45) Date of Patent: Dec. 2, 2003

(54) METHODS AND COMPOSITIONS FOR INHIBITING THE PROLIFERATION OF PROSTATE CANCER CELLS

(75) Inventor: Charles Young, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/957,045

(22) Filed: Sep. 20, 2001

(65) Prior Publication Data

US 2003/0055108 A1 Mar. 20, 2003

(51) Int. Cl.[7] ..................... A61K 31/202; A61K 31/20; A61K 31/19; A01N 37/18; A61P 13/08
(52) U.S. Cl. ..................... 514/560; 514/2; 514/211.02; 514/558; 514/573; 514/886; 424/573; 424/559; 435/7.1; 435/7.23
(58) Field of Search .................. 514/560, 2, 211.02, 514/558, 573, 886; 435/7.1, 7.23; 424/573, 559

(56) References Cited

PUBLICATIONS

Pandian et al., Fatty Acids and Prostate Cancer: Current Status and Future Challenges, J.R. Coll.Surg.Edinb., 44, Dec. 1999, pp. 352–361.*
Chung et al., Effects of docosahexaenoic acid and eicosapentaenoic acid on androgen–mediated cell growth and gene expression in LNCaP prostate cancer cells, Carcinogenesis, Aug. 2001, vol. 22, No. 8, pp. 1201–1206.*
Connolly et al., "Effects of Dietary Fatty Acids on DU145 Human Prostate Cancer Cell Growth in Athymic Nude Mice," Nutrition and Cancer, 1997, 29(2):114–119.
Denis et al., "Diet and Its Preventive Role in Prostatic Disease," European Urology, 1999, 35:377–387.
Evans, "The Steroid and Thyroid Hormone Receptor Superfamily," Science, 1988, 240:889–895.
Fradet et al., "Dietary Fat and Prostate Cancer Progression and Survival," European Urology, 1999, 35:388–391.
Gann et al., "Prospective Study of Plasma Fatty Acids and Risk of Prostate Cancer," J. Natl. Cancer Inst., 1994, 86(4):281–286.
Horoszewicz et al., "LNCaP Model of Human Prostatic Carcinoma," Cancer Res., 1983, 43:1809–1818.
Jenster, "The Role of the Androgen Receptor in the Development and Progression of Prostate Cancer," Semin. Oncol., 1999, 26(4):407–421.
Karmali et al., "The Effects of Dietary ω–3 Fatty Acids on the DU–145 Transplantable Human Prostatic Tumor," Anticancer Res., 1987, 7:1173–1180.

(List continued on next page.)

Primary Examiner—Frederick Krass
Assistant Examiner—Clinton Ostrup
(74) Attorney, Agent, or Firm—Fish & Richardson P.C., P.A.

(57) ABSTRACT

The invention provides for methods of monitoring the proliferation of cultured prostate cancer cells in the presence of omega-3 fatty acids, methods of treating an individual with prostate cancer or at risk of developing prostate cancer, and methods of reducing the risk of recurrence of prostate cancer in an individual who had previously been treated for prostate cancer. Methods of the invention further include treating an individual with benign prostatic hyperplasia (BPH) with omega-3 fatty acids as well as methods of screening for compounds that inhibit the proliferation of prostate cancer cells. The invention provides for compositions and articles of manufacture containing omega-3 fatty acids in particular formulations, and omega-3 fatty acids with a second compound that also exerts an effect on the androgen receptor.

23 Claims, 5 Drawing Sheets

OTHER PUBLICATIONS

Karmali, "Eicosanoids in Neoplasia," *Preventice Medicine*, 1987, 16:493–502.

Krongrad et al., "Androgen increases androgen receptor protein while decreasing receptor mRNA in LNCaP cells," *Mol. Cell. Endocrinol.*, 1991, 76:79–88.

Pandalai et al., "The Effects of Omega–3 and Omega–6 Fatty Acids on in Vitro Prostatic Cancer Growth," *Anticancer Res.*, 1996, 16:815–820.

Rose and Cohen, "Effects of dietary menhaden oil and retinyl acetate on the growth of DU 145 human prostatic adenocarcinoma cells transplanted into athymic nude mice," *Carcinogenesis*, 1988, 9(4):603–605.

Rose and Connolly, "Effects of Fatty Acids and Eicosanoid Synthesis Inhibitors on the Growth of Two Human Prostate Cancer Cells Lines," *The Prostate*, 1991, 18:243–254.

Rose and Connolly, "Dietary Fat, Fatty Acids and Prostate Cancer," *Lipids*, 1992, 27(10):798–803.

Rose and Connolly, "Omega–3 fatty acids as cancer chemopreventive agents," *Pharmacol. Ther.*, 1999, 83:217–244.

Tsai and O'Malley, "Molecular Mechanisms of Action of Steroid/Thyroid Receptor Superfamily Members," *Annu. Rev. Biochem.*, 1994, 63:451–486.

Wang et al., "Decreased Growth of Established Human Prostate LNCaP Tumors in Nude Mice Fed a Low–Fat Diet," *J. Natl. Cancer Inst.*, 1995, 87(19):1456–1462.

\* cited by examiner

US 6,656,969 B2

METHODS AND COMPOSITIONS FOR INHIBITING THE PROLIFERATION OF PROSTATE CANCER CELLS

FEDERALLY SPONSORED RESEARCH OR DEVELOPMENT

The U.S. Government may have certain rights in this invention pursuant to NIH grant DK41995 and Army Defense grant DAMD17-98-1-8523.

TECHNICAL FIELD

This invention relates to prostate cancer, and more particularly to methods and compositions for inhibiting the proliferation of prostate cancer cells.

BACKGROUND

The prostate gland is located between the bladder and the rectum and wraps around the urethra. The prostate is composed of glandular tissue that produces a milky fluid and smooth muscles that contract during sex and squeeze this fluid into the urethra where it mixes with other fluid and sperm to form semen. The prostate gland converts testosterone to a more powerful male hormone, dihydrotestosterone, which affects the size of the gland and plays an important role in prostate cancer.

Prostate cancer is a malignant tumor that arises in the prostate gland and can eventually spread through the blood and lymph fluid to other organs, bones, and tissues. Prostate cancer is the most commonly diagnosed cancer in the U.S., and it is the second leading cause of cancer death in American men after non-melanoma skin cancer. Although prostate cancer is just as common in Japan as in the United States, death rates from prostate cancer are significantly lower in Japan. It is unlikely that these differences are all genetic, because Japanese men who migrate to the United States die of prostate cancer with increasing frequency as a function of the number of years they reside in the United States. It is possible that this paradox could be explained, at least in part, by dietary factors.

Benign prostatic hyperplasia (BPH) is a benign enlargement of the prostate gland caused by the growth of both glandular and stromal tissues. Because the prostate enlargement in BPH is affected by testosterone, many men are concerned that it may be related to prostate cancer. A ten-year study, however, found no higher risk for prostate cancer in men with or that have experienced BPH. BPH develops in the inner zone of the prostate (i.e., predominantly stromal cells), while cancer tends to develop in the outer area (i.e., epidermal cells).

SUMMARY

It is reported herein that the transactivating ability of the androgen receptor was inhibited by omega-3 fatty acids. Accordingly, the invention provides for methods of monitoring the proliferation of cultured prostate cancer cells in the presence of omega-3 fatty acids, methods of treating an individual with prostate cancer or at risk of developing prostate cancer, and methods of reducing the risk of recurrence of prostate cancer in an individual who had previously been treated for prostate cancer. Methods of the invention further include treating an individual with benign prostatic hyperplasia (BPH) as well as methods of screening for compounds that inhibit the proliferation of prostate cancer cells. The invention provides for compositions and articles of manufacture containing omega-3 fatty acids in particular formulations, or omega-3 fatty acids with a second compound that also exerts an effect on the androgen receptor.

In one aspect, the invention provides methods of monitoring the proliferation of cultured prostate cancer cells in the presence of omega-3 fatty acid. Such a method includes contacting the prostate cancer cells with an omega-3 fatty acid and determining the transactivating ability of an androgen receptor. Generally, a decrease in the transactivating ability of the androgen receptor indicates an inhibitory effect by an omega-3 fatty acid on the proliferation of the prostate cancer cells. Representative prostate cancer cell lines include LNCaP cells or LAPC-4 cells. Representative omega-3 fatty acids include docosahexaenoic acid (DHA) and eicosapentaenoic acid (EPA).

In another aspect, the invention provides methods of treating an individual with prostate cancer or at risk of developing prostate cancer. Methods of treating an individual with prostate cancer or at risk of developing prostate cancer include identifying an individual with prostate cancer or at risk of developing prostate cancer, administering a dose of an omega-3 fatty acid to the individual that is effective to inhibit the transactivating ability of an androgen receptor, and monitoring the transactivating ability of the androgen receptor in the individual. Inhibiting the transactivating ability of the androgen receptor inhibits the proliferation of prostate cancer cells, thereby treating the individual. For example, an omega-3 fatty acid can be administered to a human, and in an amount of from about 5 mg/kg to about 25 mg/kg. An omega-3 fatty acid can be administered orally, transdermally, intravenously, intraperitoneally, or using an implant.

In still another aspect, the invention provides for methods of reducing the risk of recurrence of prostate cancer in an individual who previously had been treated for prostate cancer. Such a method includes the step of administering a dose of an omega-3 fatty acid to the individual that is effective to inhibit the transactivating ability of an androgen receptor. The method can further include the step of monitoring the transactivating ability of the androgen receptor in the individual. Generally, inhibiting the transactivating ability of the androgen receptor inhibits the proliferation of prostate cancer cells, and thereby reduces the risk of recurrence of prostate cancer in the individual. The individual may have previously undergone a radical prostectomy.

In yet another aspect, the invention provides methods of treating an individual with benign prostatic hyperplasia (BPH). This method includes identifying an individual with BPH, and administering a dose of an omega-3 fatty acid to the individual that is effective to inhibit the transactivating ability of an androgen receptor. The method also can include monitoring the transactivating ability of the androgen receptor in the individual. Inhibiting the transactivating ability of the androgen receptor thereby treats the BPH in the individual.

The invention additionally provides methods of screening for compounds that inhibit the proliferation of prostate cancer cells, including contacting prostate cancer cells with a compound, and determining the transactivating ability of an androgen receptor. The method also can include monitoring the transactivating ability of the androgen receptor in the prostate cancer cells. Decreased transactivating ability of the androgen receptor in the prostate cancer cells compared to prostate cancer cells not contacted with the compound indicates a compound that inhibits the proliferation of prostate cancer cells. Prostate cancer cells such as LNCaP cells or LAPC-4 cells can be used in this method.

Further, the invention provides compositions that include an omega-3 fatty acid, one or more compounds having a particular mechanism of action (i.e., inhibiting expression of a gene encoding an androgen receptor, inhibiting nuclear localization of an androgen receptor, and inhibiting the transactivating ability of an androgen receptor) and a pharmaceutically acceptable carrier. Representative examples of compounds having such particular mechanisms of action include silymarin, silibin, quercetin, perillyl alcohol (POH) of a derivative thereof, resveratrol, flufenamic acid, tea polyphenols, and anti-androgen compounds. It is a feature of the invention to provide such a composition in the form of an article of manufacture (e.g., a kit). Such an article of manufacture can include packaging material comprises instructions for using the composition to inhibit the transactivating ability of an androgen receptor in an individual.

In another aspect of the invention, there are provided compositions that include an omega-3 fatty acid and that are formulated for transdermal delivery to the prostate of an individual. Delivery to the prostate typically inhibits the transactivating ability of an androgen receptor. In addition, the invention provides compositions that include an omega-3 fatty acid and that are formulated for implantation near the prostate of an individual. Generally, implantation near the prostate inhibits the transactivating ability of an androgen receptor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Figure 1:
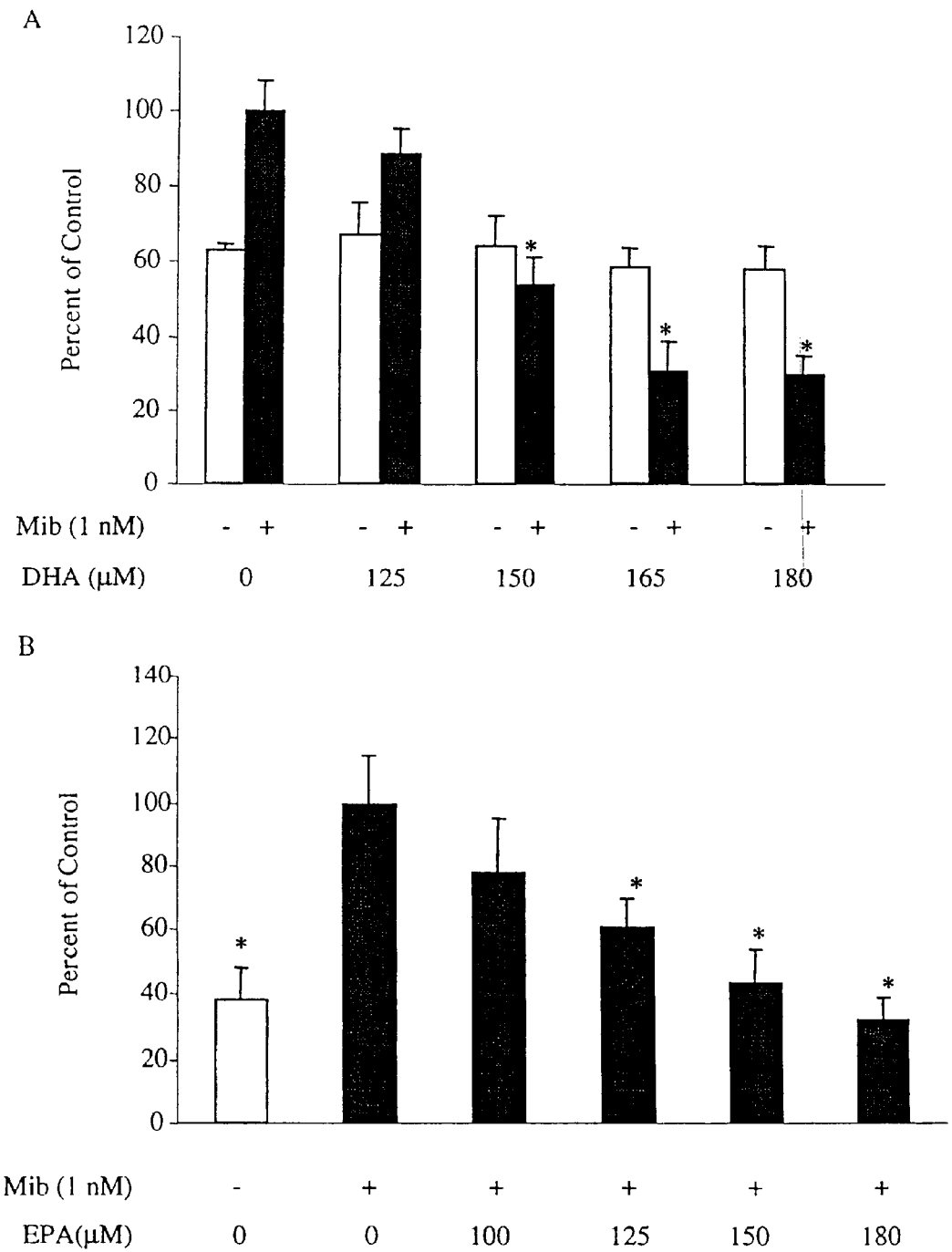
FIG. 1 demonstrates the effects of DHA (FIG. 1A) or EPA (FIG. 1B) on androgen stimulated-growth responses in LNCaP cells. *Depicts significant inhibition compared to the no treatment control in FIG. 1A and compared to the Mib treated in FIG. 1B.

It is reported herein that the transactivating activity of the androgen receptor was inhibited by omega-3 fatty acids. Accordingly, the invention provides for methods of monitoring the proliferation of cultured prostate cancer cells in the presence of omega-3 fatty acids, methods of treating an individual with prostate cancer or at risk of developing prostate cancer, and methods of reducing the risk of recurrence of prostate cancer in an individual who had previously been treated for prostate cancer. The invention further includes methods treating an individual with benign prostatic hyperplasia (BPH) as well as methods of screening for compounds that inhibit the proliferation of prostate cancer cells. The invention provides for compositions and articles of manufacture containing omega-3 fatty acids in particular formulations, or omega-3 fatty acids with a second compound that also exerts an effect on the androgen receptor.

It was shown herein that omega-3 fatty acids inhibited androgen-stimulated induction of prostate-specific antigen (PSA). The invention provides a novel aspect of omega-3 fatty acids in that omega-3 fatty acids can attenuate androgen receptor-mediated transactivation of prostate cancer-specific genes in androgen-responsive prostate cancer cells. Thus, the invention provides for methods of preventing or treating prostate cancer using omega-3 fatty acids.

There is epidemiological support for a protective influence of omega-3 fatty acid against prostate cancer. Japanese and Alaskan Eskimo men who eat large quantities of fish have a low risk for prostate cancer. Fish traditionally provide the major source of animal proteins and fat for Japanese and Eskimo people. Fish oil is rich in omega-3 fatty acids. Epidemiological studies demonstrated a correlation between large consumption of animal fat and death from prostate cancer. Animal fat contains high amounts of omega-6 fatty acids. A study of American men showed a positive association between α-linoleic acid (an omega-6 fatty acid) in the diet and prostate cancer.

The Androgen Receptor and Prostate Cancer

Androgens play an important role in the proliferation, differentiation, maintenance, and function of the prostate. The androgen receptor is the essential mediator for androgen action and is a ligand-dependent transcription factor belonging to the nuclear steroid hormone receptor superfamily. Androgens can enhance androgen receptor protein levels by increasing the half-life, as well as by stimulating the phosphorylation of the androgen receptor. Phosphorylation may affect numerous characteristics of nuclear receptors including ligand binding, nuclear translocation, dimerization, DNA binding, and protein—protein interactions.

Evidence shows that androgens are also involved in the development and progression of prostate cancer. Therefore, the androgen receptor also plays a critical role in the development of prostate cancer, in part due to overstimulation of the receptor by androgens. Prostate cancer also has been attributed to altered transactivation activities of the receptor or to mutations in the androgen receptor that, for example, enable the receptor to respond to non-androgen steroids. The androgen receptor can be expressed in all stages of prostate cancer, and at least one-third of advanced prostate cancers contain amplified androgen receptor genes.

The utilization of androgen deprivation as a treatment for advanced prostate cancer was first demonstrated in 1941 and has become a standard treatment. Based on the morbidity associated with ablation of the adrenal glands, castration alone was the gold standard until the 1980s, when anti-androgen agents, including cyproterone acetate, megestrol acetate, and flutamide, were developed to compete with androgen for binding to the androgen receptor. Many new classes of drugs that interfere with androgen production and function have been identified.

In spite of the apparent regression of tumors by hormone therapy, however, prostate cancer often recurs within 3 years and becomes hormone refractory with a potentially fatal outcome. Many molecular mechanisms have been postulated to be responsible for the development of recurrent hormone-refractory tumors with most involving alterations in the function of the androgen receptor and its complex signaling pathways. The androgen receptor can be activated by a number of growth factors or cytokines in the absence of androgens or by low levels of androgens or other non-androgenic steroid hormones after hormone therapy. That the majority of hormone-refractory cancers still express the androgen-responsive prostate-specific antigen PSA is a protein secreted by the epithelial cells of the prostate gland, including prostate cancer cells. An abnormally high level of PSA is indicative of abnormal prostate cells. (PSA) gene indicates that the androgen receptor signaling pathway is functional.

Nucleic acid sequences encoding androgen receptors have been cloned and sequenced from numerous organisms. Representative organisms and GenBank accession numbers for androgen receptor sequences therefrom include the following: frog (*Xenopus laevis*, U67129), mouse (*Mus musculus*, 109558), rat (*Rattus norvegicus*, 292896), human (*Homo sapiens*, 105325), rabbit (*Oryctolagus cuniculus*, 577829), cow (*Bos taurus*, Z75313, Z75314, Z75315), canary (*Serinus canaria*, 414734), and whiptail lizard (*Cnemidophous uniparens*, 1195596). Additionally, Cancer Genetics Web (www.cancer-genetics.org) contains database entries for wild-type and mutant androgen receptor sequences.

Omega-3 Polyunsaturated Fatty Acids

Omega-3 polyunsaturated fatty acids, also known as α-linolenic acid, are required for many important cellular processes including cell proliferation and differentiation. Omega-3 fatty acids are essential because the body cannot manufacture them from other substances or compounds. Omega-3 fatty acids are capable of lowering triglyceride levels, decreasing blood pressure, and reducing platelet reactivity. Omega-3 fatty acids offer protective effects against coronary heart disease, stroke, hypertension, and inflammatory and autoimmune disorders. Omega-3 fatty acids can also exert a beneficial influence on vascular walls. The therapeutic effect of omega-3 fatty acids can be attributed to inflammation-inhibiting properties, and to the fact that omega-3 fatty acids have an inhibiting influence on the biological activity of thromboxane, a substance that, among other things, is a potent vasoconstrictor.

Omega-3 fatty acids, typically in the form of fish oil preparations, have shown success in (a) protecting against the relapse of Crohn's disease; (b) decreasing the risk of preeclampsia during pregnancy; (c) reducing the symptoms of dysmenorrhea; (d) treating kidney disorders; (e) preventing depression; (f) improving the pain score of patients having rheumatoid arthritis; and (g) reducing the risk of a primary cardiac arrest. Some of the favorable effects of omega-3 fatty acids specifically important in the prevention and treatment of kidney diseases are, among others, vasodilatation, inhibition of inflammatory reactions, a decrease of platelet aggregation and a reduction of blood viscosity. The protective effect of omega-3 fatty acids on the kidneys extends to individuals who are treated with cyclosporine, a nephrotoxic immunosuppressive agent used to suppress autoimmune diseases and to prevent the rejection of transplanted organs.

Methods of Monitoring and Inhibiting the Proliferation of Prostate Cancer Cells

The invention provides for methods of monitoring the proliferation of prostate cancer cells. According to the methods of the invention, the proliferation of prostate cancer cells can be monitored by first contacting those cells with omega-3 fatty acids and then determining the transactivating ability of the androgen receptor. The transactivating ability of the androgen receptor can be determined using conventional methods (e.g., methods described herein). A decrease in the transactivating ability is indicative of an inhibitory effect by omega-3 fatty acids on the proliferation of the prostate cancer cells. Proliferation of prostate cancer cells as used herein refers to an increase in the number of prostate cancer cells (in vitro or in vivo) over a given period of time (e.g., hours, days, weeks, or months). It is noted that the number of prostate cancer cells is not static and reflects both the number of cells undergoing cell division and the number of cells dying (e.g., by apoptosis). An inhibition of the proliferation of prostate cancer cells can be defined as a decrease in the rate of increase in prostate cancer cell number, a complete loss of prostate cancer cells, or any variation therebetween. With respect to tumors, a decrease in the size of a tumor can be an indication of an inhibition of proliferation.

Prostate cancer cells that can be maintained in culture and are useful in the invention include without limitation LNCaP cells and LAPC-4 cells. The LNCaP cell line is an established androgen-responsive prostate cancer cell line obtained from a lymph node metastasis of a prostate cancer patient. LNCaP cells express the androgen receptor and a number of androgen-inducible genes such as PSA, human glandular kallikrein (hK2), NKX3.1 and omithine decarboxylase (ODC). The gene encoding the androgen receptor in the LNCaP cell line contains a mutation in its ligand binding domain, but otherwise is functional. LAPC-4 cells, another androgen-responsive prostate cancer cell line suitable for use in the invention, expresses a wild-type androgen receptor. LAPC-4 cells additionally express PSA and hK2, which are up-regulated in the LAPC-4 cells by androgens. Other prostate cancer cell lines are available and include PC-3 and DU145.

The invention further provides for methods of treating an individual with prostate cancer or at risk of developing prostate cancer. An individual is first identified as having prostate cancer or being at risk for developing prostate cancer and then administered an effective dose of omega-3 fatty acids. The transactivating ability of the androgen receptor can be monitored in the individual to evaluate the effects of omega-3 fatty acids on prostate cancer cells. Generally, an inhibition of the transactivating ability of the androgen receptor by omega-3 fatty acids inhibits the proliferation of prostate cancer cells, thereby treating the individual.

Prostate cancer cells can be identified using several criteria. Prostate cancer cells in culture (e.g., LNCaP cells) can be characterized by the response of such cells to androgens or androgenic agonists or antagonists. Molecular markers, such as increased or decreased expression of androgen-regulated genes or genes involved in prostate cancer (e.g., PSA, hk2, c-jun, ODC, and NKX3.1) also can be used to characterize prostate cancer cells in culture. Prostate cancer in vivo can be identified by a digital rectal examination of a patient, or by imaging or scanning techniques (e.g., magnetic resonance imaging (MRI), or prostascint scans). In addition, the degree of cellular differentiation can be evaluated in prostate cancer cells from an individual, typically removed via a biopsy of prostate tissue, using a Gleason score. Further, there are several commercially available diagnostic tests for PSA and PSA-II (e.g., Roche Diagnostics Inc., Indianapolis, Ind.) to screen individuals for prostate cancer and to monitor individuals undergoing treatment for prostate cancer. Prostate cancer can be staged, for example, using a Partin Table and/or a Partin II Table (see Partin et al., 1994, *Urology*, 43:649–59 and http://www.theraseed.com/gloss.html for more information).

For the purpose of this invention, omega-3 fatty acids can be administered orally, transdermally, intravenously, intraperitoneally, or by implantation. The route of administration typically depends on a variety of factors, such as treatment environment and therapeutic goals. Administration of omega-3 fatty acids can be on a continuous or an intermittent basis. In addition, preparations for administration of omega-3 fatty acids can be suitably formulated to give controlled release of the compound. Preparations for intravenous and intraperitoneal administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, as well as alcohol, saline, and buffered solutions. Other additives such as, for example, antimicrobials, anti-oxidants, chelating agents, inert gases, steroids, anti-inflammatory agents, immunosuppressants, vasodilators, vasoconstrictors, and the like may also be present.

Tablets or capsules for oral administration can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Liquid preparations for oral administration can take the form of, for example, solutions, syrups or suspension, or they can be presented as a dry product for constitution with saline or other suitable liquid vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl- or propyl-p-hydroxybenzoates or sorbic acid). The preparations can also contain buffer salts, flavoring, coloring and sweetening agents as appropriate.

Preparations for transdermal administration are known in the art. Such transdermal preparations can be in the form of a scrotum patch or a patch for application on the back, abdomen, thighs or buttocks. A transdermal patch typically includes a soft flexible backing (e.g., polyester or polyester/ethylene-vinyl acetate copolymer), a reservoir (in some cases, the compound or composition, e.g., omega-3 fatty acids, can be deposited as a film on the ethylene-vinyl acetate copolymer or can be combined with, for example, alcohol and a gelling agent such as hydroxypropyl cellulose), and an adhesive backing made out of, for example, polyisobutylene and colloidal silicon dioxide (usually with a removable liner (e.g., silicone-coated polyester, or fluorocarbon diacrylate) to protect the adhesive until the patch is applied). A transdermal patch also can contain a formulation (e.g., polyisobutylene adhesive) to control the rate of release of the compound or composition.

Implantable devices are known in the art and can be in the form of a pellet or a seed containing or coated with a compound or composition, e.g., omega-3 fatty acids. A pellet or seed can be a metal alloy (e.g., cobalt, or palladium) or an inert plastic or other substance. A device for implantation in or near the prostate can be delivered using a delivery catheter (similar to brachytherapy) and can be deposited in or near the prostate transperineally, transrectally, or transurethrally. A transrectal ultrasound can be used in conjunction with implantation to visualize and image the prostate and the positioning of the implantable device.

According to the invention, an effective dose of omega-3 fatty acids is an amount that inhibits the transactivating ability of the androgen receptor, thereby inhibiting the proliferation of prostate cancer cells. Inhibition of the transactivating ability of the androgen receptor and the subsequent inhibition of the proliferation of prostate cancer cells can be determined using methods and assays described herein. It is anticipated that an effective dose of omega-3 fatty acids is from about 5 mg of omega-3 fatty acids per kg weight of the individual (mg/kg) to about 25 mg/kg. Toxicity and therapeutic efficacy of different doses of omega-3 fatty acids can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio of $LD_{50}/ED_{50}$. Doses of omega-3 fatty acids that exhibit high therapeutic indeces are preferred. An effective dose of omega-3 fatty acids can be delivered in a single dose or as multiple doses over a period of time.

The transactivating ability of the androgen receptor can be examined by evaluating the expression of genes whose transcription is regulated by androgen receptor binding. Such genes include PSA, h2k, NKX3.1, and ODC. The amount of transcript and/or protein of such genes in the presence and absence of the compound can be readily determined using art-routine methods such as those described herein. Alternatively, prostate cancer cells in culture can be made transgenic for one or more androgen-regulated genes and the expression of such transgenes can be evaluated in the presence and absence of a compound.

In addition, the invention provides methods of reducing the risk of recurrence of prostate cancer in an individual that previously had undergone treatment for prostate cancer. Such methods include administering an effective dose of omega-3 fatty acids to the individual such that the transactivating ability of the androgen receptor is inhibited. Inhibiting the transactivating ability of the androgen receptor inhibits the proliferation, and therefore the recurrence, of prostate cancer cells. Treatments for prostate cancer that an individual might undergo include hormone therapy, chemotherapy, radiation therapy and, oftentimes, a prostatectomy, in which part of all of the prostate gland is removed. A radical prostatectomy includes removal of the entire prostate as well as the seminal vesicles. Due to a high incidence of prostate cancer recurring, even following such treatments (including a radical prostatectomy), methods of the invention provide for administration of omega-3 fatty acids during or following such treatments. Administration of omega-3 fatty acids may be particularly useful following a radical prostatectomy.

The invention additionally provides for a method of treating an individual with benign prostatic hyperplasia (BPH). Individuals with BPH may present with prostatitis and/or difficulty urinating, and an enlarged prostate due to BPH is typically palpable during a digital rectal exam. Methods of the invention include identifying an individual with BPH, and administering a dose of omega-3 fatty acids to said individual effective to inhibit the transactivating ability of an androgen receptor. Such an inhibition of the androgen receptor's transactivating ability reduces the androgen receptor-mediated growth response and thereby treats the individual with BPH.

Methods of Screening Compounds

The invention provides for methods of screening for compounds that inhibit the proliferation of prostate cancer cells by decreasing the transactivating ability of the androgen receptor. Screening methods are one of the fundamental tools used in molecular biology for rapid and efficient evaluation of compounds. Screening methods of the invention include contacting prostate cancer cells with a compound under conditions and for a time sufficient to allow the compound to enter the cell, and determining the transactivating ability of the androgen receptor. Generally, decreased transactivating ability of the androgen receptor in cells compared to cells not contacted with the compound indicates a compound that inhibits the proliferation of prostate cancer cells. Such compounds can be evaluated using prostate cancer cells in culture, such as LNCaP or LAPC-4 cells, or can be evaluated using a cell-free system.

Methods of determining the transactivating ability of the androgen receptor are described above. Expression of a gene encoding an androgen receptor in prostate cancer cells can be examined in the presence and absence of a compound using Northern blot analysis (to evaluate transcription) and/or Western blot analysis (to evaluate translation). Techniques to isolate RNAs and proteins from cells as well as methods of separation (e.g., electrophoretically) are well known and routine in the art. Androgen receptor mRNA can be detected by hybridization with a labeled oligonucleotide probe that is complementary to a portion of the androgen receptor transcript. Androgen receptor proteins can be detected by contacting proteins from a cell with a labeled agent that selectively binds to the androgen receptor protein. Conditions for allowing and detecting hybridization of nucleic acids or binding of antibodies to proteins are well known in the art. Antibodies that have binding affinity to androgen receptor proteins are commercially available (e.g., from Research Diagnostics Inc. (Flanders, N.J.) and Alpha Diagnostic International (San Antonio, Tex.)). The term "label", with regard to an oligonucleotide probe or an antibody is intended to encompass direct labeling of the oligonucleotide or antibody by coupling a detectable substance to the oligonucleotide or antibody, as well as indirect labeling of the oligonucleotide or antibody by reactivity with a detectable substance. Examples of labels and detectable substances are well known in the art. Additional methods to detect androgen receptor mRNA (e.g., RT-PCR or dot blots) or protein (e.g., immunoassays or chromatography) are well known and also practiced routinely in the art.

The ability of the androgen receptor to translocate to the nucleus also can be evaluated in the presence and absence of a compound to determine if the compound inhibits the nuclear localization of the androgen receptor. Nuclei are typically isolated using an appropriate gradient such as a sucrose gradient, a percol gradient, or the like. The nuclei can be lysed (for example, by exposure to sonication, or ultrasound waves) and androgen receptor protein can be detected using routine methods such as Western blotting. Nuclear translocation also can be examined using, for example, immunocytochemistry to identify androgen receptor protein in the nucleus and/or outside of the nucleus.

In addition, the amount of c-jun protein can be evaluated as an indicator of androgen receptor activity. When overexpressed, c-jun has been shown to inhibit the transactivating ability of the androgen receptor. c-jun is a partner with c-fos in the transcription factor AP-1. Increased evidence suggests that the function of the androgen receptor may be affected by an interaction with AP-1.

Compositions and Articles of Manufacture

The invention provides compositions that include omega-3 fatty acids or a derivative thereof and at least one other compound selected for its particular mechanism of action on the androgen receptor. The mechanism of action exerted by the other compound(s) can be one or more of the following: inhibition of the expression of a gene encoding an androgen receptor; inhibition of the nuclear localization of an androgen receptor; or inhibition of the transactivating ability of an androgen receptor. Representative compounds exhibiting such mechanisms of action include the following: POH, and resveratrol (transactivating ability); silymarin (nuclear localization); flufenamic acid, tea polyphenols (e.g., (−)-epigallocatechin gallate (EGCG)), and quercetin (expression); and numerous anti-androgen compounds (e.g., bicalutamide, flutamide, nilutamide, or cyproterone).

Compositions containing omega-3 fatty acids can be formulated for delivery to the prostate. In one aspect, omega-3 fatty acids are formulated for transdermal delivery to the prostate. In another aspect, compositions containing omega-3 fatty acids can be formulated for implantation in or near the prostate. Delivery of compositions containing omega-3 fatty acids directly to the prostate of an individual inhibits the transactivating ability of the androgen receptor. Formulations for administration of omega-3 fatty acids described above and apply as well to the disclosed compositions containing omega-3 fatty acids.

A composition containing omega-3 fatty acids can be in any form provided the composition can be administered to an individual in an amount and for a duration effective to inhibit the transactivating ability of the androgen receptor gene, thereby inhibiting the proliferation of prostate cancer cells. Pharmaceutically acceptable carriers include solvents, dispersion media, coatings, antibacterial and anti-fungal agents, isotonic and absorption delaying agents and the like, appropriate to specific routes of administration.

Omega-3 fatty acids compositions of the invention that are effective for inhibiting transactivating ability of the androgen receptor as described herein can be combined with packaging material and sold as a kit (i.e., an article of manufacture). Components and methods for producing articles of manufactures are well known. In addition to a composition containing articles of manufacture can include oligonucleotide probes, antibodies, and/or other useful agents for determining the transactivating ability of the androgen receptor. Instructions describing how the composition can be used for inhibiting the transactivating ability of the androgen receptor to thereby inhibit the proliferation of prostate cancer cells can be included in such kits.

In accordance with the present invention, there may be employed conventional molecular biology, microbiology, biochemical and recombinant DNA techniques within the skill of the art. Such techniques are explained fully in the literature. The invention will be further described in the following examples, which do not limit the scope of the invention described in the claims.

EXAMPLES

Example 1

Cell Culture, Cell Proliferation Assays, and PSA Quantification Assays

A human prostate cancer cell line, LNCaP (American Type Culture Collection (ATCC), Manassas, Va.), was cultured in RPMI 1640 medium (Mediatech, Herndon, Va.) supplemented with 5% fetal bovine serum (FBS) at 37° C. and 5% $CO_2$ until reaching approximately 50–70% confluence. The media were changed to serum-free RPMI 1640 24 hrs prior to experiments being performed to deplete undesired steroids. Cells were then treated with RPMI 1640 containing 5% charcoal-stripped FBS and cis-4, 7, 10, 13, 16, 19-docosahexaenoic acid (DHA) or cis-5, 8, 11, 14, 17-eicosapentaenoic acid (EPA) (Sigma, St. Louis, Mo.) dissolved in ethanol at designated concentrations with or without mibolerone (Mib) (New England Nuclear, St. Louis, Mo.), a non-metabolizable synthetic androgen, dissolved in ethanol. Equivalent amounts of solvent were added to control cells.

For cell proliferation and PSA expression assays, LNCaP cells were seeded at $2 \times 10^4$ cells per well in 24 well plates. After 72 hrs, cells were treated with serum-free RPMI 1640 for 24 hrs and then incubated with varying amounts of DHA and EPA with or without 1 nM Mib in media containing 5% charcoal-stripped serum. Six days after treatment, 400 $\mu$l of spent media were collected for total PSA protein measurements by the Tandem-E PSA kit (Hybritech Inc. San Diego, Calif.). An MTS assay was performed (Promega, Madison, Wis.) for measuring cell viability. Four wells per treatment were used for the above assays and it was repeated twice. PSA levels in spent media were normalized to cell number.

Example 2

Transient Transfection/Assays

LNCaP or PC-3 cells were plated in 60 mm dishes. Cells were transiently transfected as described (Zhang et al., 1999, Endocrin, 140:1665–71) with either 3 copies of an hK2 ARE in a pGL3 promoter plasmid, CMV-β-gal, a human androgen receptor expression vector or a c-jun expression vector as indicated. The androgen receptor and c-jun constructs were driven by an SV40 promoter. LNCaP cells were transfected using liposome containing dimethyldioctadecyl-ammonium bromide (DDAB) (Sigma) and L-α-lecithin (Sigma) (4:10 w/w) and PC-3 cells were transfected using lipofectamine (Gibco BRL, Grand Island, N.Y.). After 24 hrs, LNCaP cells were treated with 150 $\mu$M DHA or EPA with or without 3.2 nM Mib. Whole cell extracts were prepared according to Ren et al., (2000, Oncogene, 19:1924–32) and a luciferase assay was performed according to manufacturer's instructions (Promega). The CMV-β-galactosidase (β-gal) expression vector and the parental vector (pGL3) were included as controls in the above transfections. β-gal activity or total protein using the Bradford assay (BioRad, Hercules, Calif.) were assayed for normalization purposes. Luciferase activities were normalized to β-gal activities and presented as relative light units/mU β-gal. Each transfection was done three times and results were analyzed by the Student's t-test. A $p<0.05$ was accepted as the level of significance.

Example 3

Northern Blot and Western Blot Analysis

After steroid depletion as described in Example 1 above, LNCaP cells were treated with varying amounts of DHA and 1 nM Mib as indicated and RNA was collected using the guanidine isothiocyanate method (Chomczynski et al., 1987, Anal. Biochem., 162:156–9). A denaturing RNA gel was run and transferred onto a nylon membrane (BioRad) according to the GeneScreen protocol (New England Nuclear). Fifteen $\mu$g of total RNA was loaded in each lane. cDNAs for PSA, ornithine decarboxylase (ODC), NKX 3.1, fkbp 51, Drg-1 and glyceraldehyde-3-phosphate dehydogenase (GAPDH) were labeled with $[P^{32}]dCTP$ by random priming and used as probes. The hybridizations were performed according to the recommended protocol using ExpressHyb Hybridization Solution (Clontech, Palo Alto, Calif.). The films were autoradiographed at −70° C. overnight.

For Western blotting, LNCaP cells were plated in 10 cm dishes at $9 \times 10^5$ cells per dish in RPMI 1640 (Mediatech, Herndon, Va.) and 5% FBS (Biofluids, Rockville, Md.). After steroid depletion as described in Example 1 above, the cells were treated with 1 nM Mib and varying concentrations of DHA and EPA. Cells were collected at designated times for whole cell protein preparation according to manufacturer's instructions (Santa Cruz, Santa Cruz, Calif.). Protein levels were measured with a BioRad DC protein assay (BioRad, Hercules, Calif.). Fifteen $\mu$g of protein were loaded into precast 4–12% NuPage gels (Novex, San Diego, Calif.), run with MOPS buffer, and transferred according to the manufacturer's instructions onto a nitrocellulose membrane (BioRad). Ponceau S was added to the membranes and visualized with a digital camera and used as a loading and transfer control. The membranes were blocked overnight at 4° C. in TBST (20 mM Tris-HCl (pH 8.0), 137 mM NaCl, and 0.1% Tween 20) and 5% dry milk. The membranes were washed 3 times for 10 min each with TBST. Primary antibody for the androgen receptor (Pharmingen, San Diego, Calif.) at a 1:1000 dilution or for c-jun (Calbiochem, La Jolla, Calif.) at a 1:500 dilution were incubated at room temperature for 1 hr. The membranes were washed 3 times for 10 min each with TBST. An appropriate horseradish peroxidase (HRP) secondary antibody (Amersham, Piscataway, N.J.) at a 1:10000 dilution was also incubated for 1 hr at room temperature. The membranes were washed again once for 10 min and Renaissance chemiluminescence (New England Nuclear, Boston, Mass.) was used according to the manufacturer's instructions. β-tubulin was detected by specific β-tubulin antibody (1:1000, Sigma) was also used as the control for protein loading and transfer efficiency.

Example 4

Effect of DHA and EPA on the Androgen Receptor

The effects of DHA and EPA on androgen-stimulated growth were examined in LNCaP cells. DHA treated cells with mibolerone (Mib) showed a dose-dependent statistically significant decrease in cell growth ($p<0.05$). DHA-treated cells without androgen stimulation, however, showed little response, suggesting that DHA inhibits the androgen-mediated growth response. Androgens further potentiated the inhibitory effect of DHA (FIG. 1A). Similarly, EPA treatment decreased androgen-stimulated cell growth, but with little or no additional effect by androgens (FIG. 1B).

Figure 2:
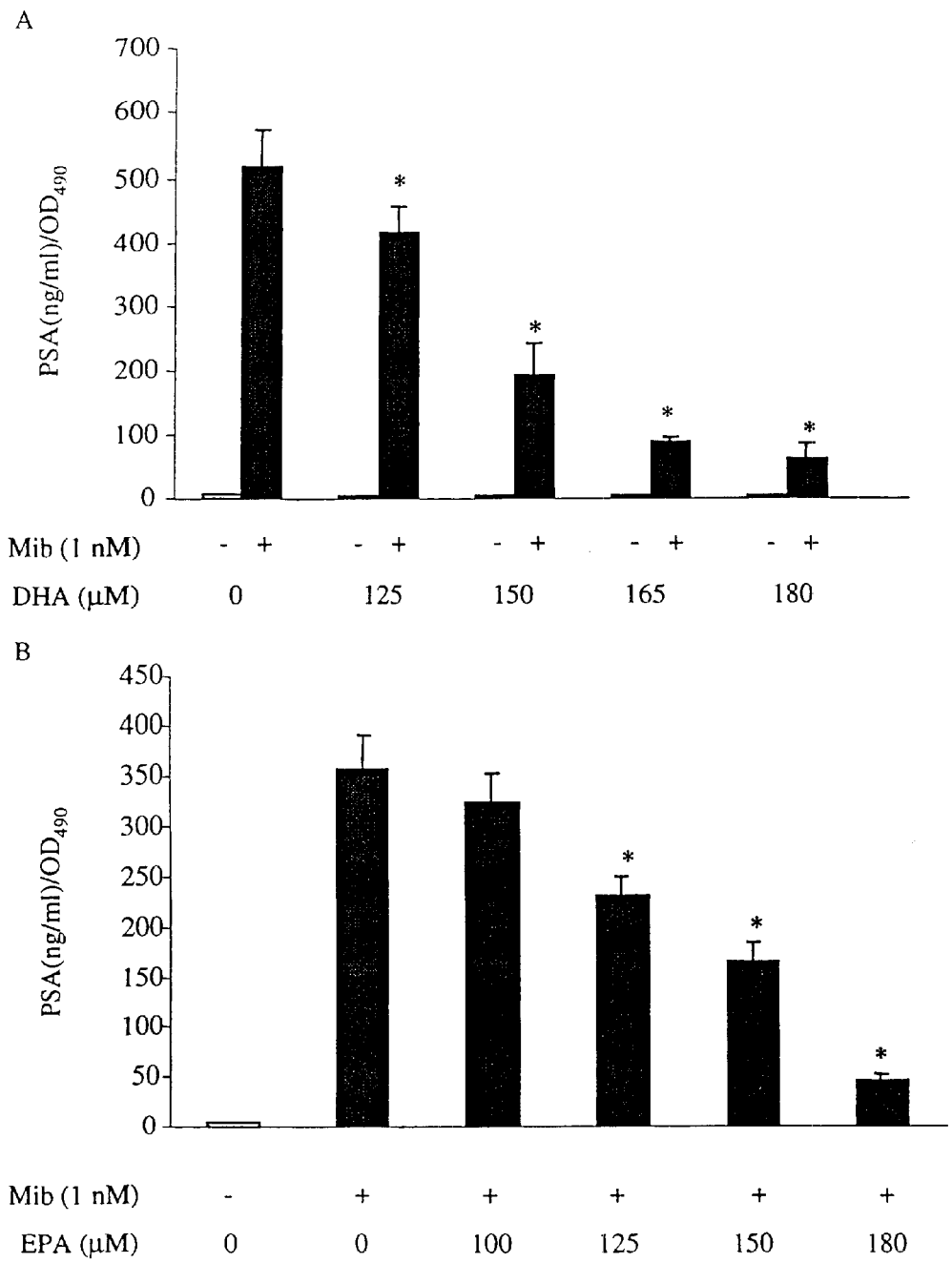
FIG. 2 depicts the androgen-induced expression of PSA protein in LNCaP cells in the presence of DHA (FIG. 2A) or EPA (FIG. 2B). *Depicts significant inhibition compared to the no treatment controls.

To further examine the effects of DHA or EPA on androgen action in LNCaP cells, expression of an androgen-regulated gene, PSA, was examined. The normalized data in FIG. 2A shows the decrease in androgen-stimulated PSA secretion in the presence of DHA. FIG. 2B with EPA treatment demonstrates a similar pattern as FIG. 2A, but EPA treatment required higher EPA concentrations for significant inhibition. Similar effects were seen on the expression of another androgen-regulated gene, hK2.

Northern analysis was performed to examine the expression of several androgen-regulated genes following DHA treatment. The androgen responsive genes NKX 3.1, ornithine decarboxylase (ODC), fkbp 51, Drg-1 and PSA were examined. All mRNAs examined were induced by androgens and treatment with DHA at a concentration of 150 μM or higher greatly inhibited the androgen-induced response.

Figure 3:
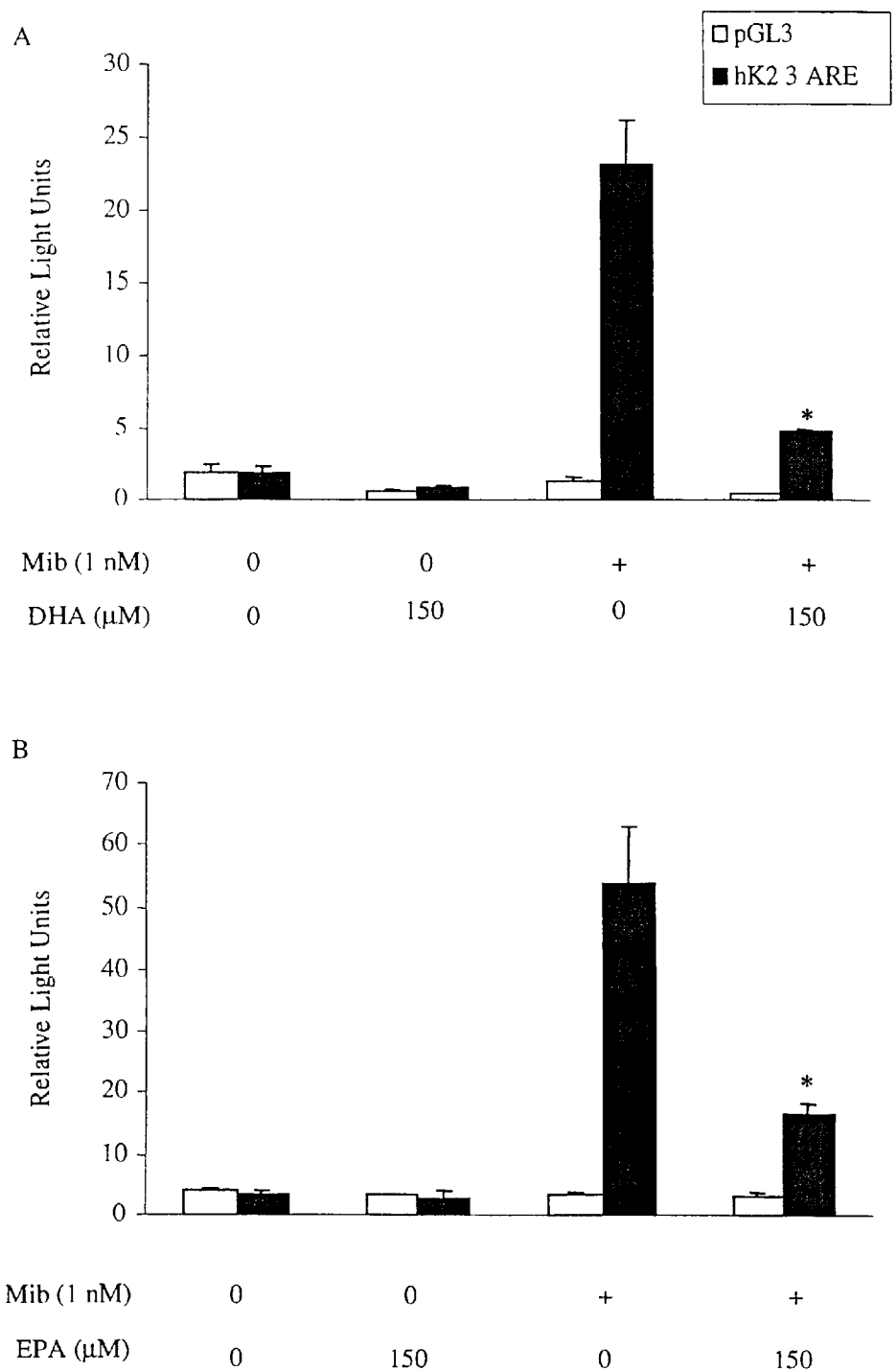
FIG. 3 demonstrates the effects of DHA (FIG. 3A) and EPA (FIG. 3B) on the androgen receptor-mediated transcription of pGL3 SV40-3 ARE or PGL3 SV40. *Depicts significant inhibition compared to the no treatment controls.

Given that all the androgen-inducible genes tested were inhibited at the mRNA level, the androgen receptor-mediated transactivation of androgen-regulated genes was examined in the presence of DHA and EPA. A construct containing three copies of an androgen responsive element in front of a luciferase reporter gene was transfected into LNCaP cells with or without Mib to test whether DHA or EPA can directly affect androgen receptor-mediated transcriptional activity. FIG. 3 shows the activity of the cells treated with DHA or EPA in the presence or absence of Mib. In the Mib treated cells, the ARE gives a strong androgenic induction of luciferase activity. However, DHA and EPA treatments significantly inhibit this androgenic response ($p<0.05$).

Furthermore, Western blot analysis for androgen receptor protein was performed to determine whether the lipids have an effect on the expression of the androgen receptor. Androgen receptor protein levels were increased by androgens and were not changed at 24 or 36 hrs following DHA or EPA treatments.

Figure 4:
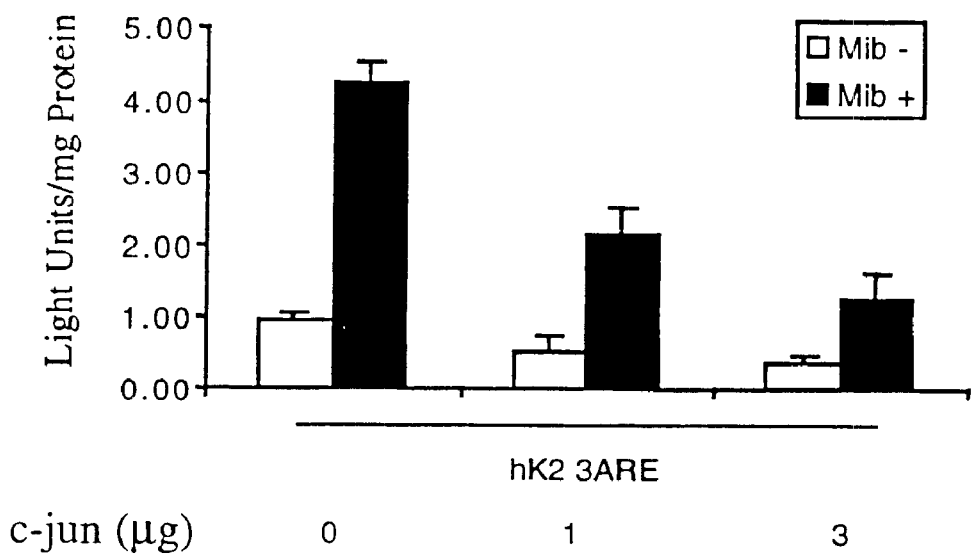
FIG. 4 shows the effects of DHA treatment on the level of c-jun protein.

To further examine the inhibition of the androgen receptor in the presence of DHA or EPA, the levels of c-jun and c-fos were determined. FIG. 4 shows that the level of c-jun protein increased with DHA treatment up to 3.5 times the level without DHA treatment. The graph depicts the data normalized to Ponceau S staining as a percent of controls. This experiment was repeated twice and representative data is shown. The levels of c-fos, however, were unaltered by treatment with DHA.

Figure 5:
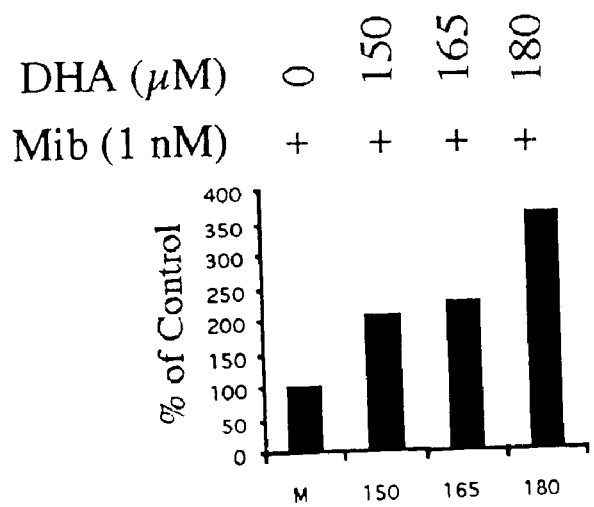
FIG. 5 demonstrates the effects of c-jun on the transcriptional activity of the androgen receptor.

It was known that overexpression of c-jun protein inhibits the function of the androgen receptor. Therefore, a transient transfection was performed to examine the effects of c-jun expression on androgen receptor function. The hK2 3 ARE construct, an androgen receptor expression vector, and a c-jun expression vector were co-transfected into PC-3 cells lacking an androgen receptor. FIG. 5 demonstrates that increasing amounts of c-jun caused a decrease in androgen-induced activities of the ARE-containing construct.

DHA decreased androgen stimulated LNCaP cell growth. Furthermore, androgenic induction of five androgen-regulated genes was significantly repressed by DHA at the steady mRNA levels. Gene transfer experiments demonstrated that DHA repressed the androgenic up-regulation of at least the PSA and hK2 genes at the transcriptional level. Similarly, EPA was able to reduce both the mRNA and protein levels corresponding to these two androgen-regulated genes.

The function of nuclear receptors like the androgen receptor can be affected by their expression levels, phosphorylation, dimerization, nuclear localization, ligand bindings, interaction capability with various proteins such as heat shock proteins (e.g., hsp70 and hsp90), and/or co-activators and other cross-talking factors. Androgens can stabilize the androgen receptor and hence increase androgen receptor levels. DHA does not seem to be able to reduce androgen receptor protein levels, although androgen receptor function is inhibited. Western blot analysis of the androgen receptor shows that DHA also did not interfere with the androgen-mediated stabilizing effect. In addition, the effect of DHA or EPA on the levels of hsp70 and hsp90 as well as the androgen receptor specific co-activator, ARA70, were examined but no inhibitory effects were observed.

Since the androgen receptor protein levels were unaffected by DHA and EPA treatments, but the androgen receptor function was clearly affected, the levels of c-jun and c-fos were examined. The AP-1 transcription factors are composed of c-fos and/or c-jun nuclear proteins and can act as cross-talking factors for the androgen receptor. There is increased evidence that androgen receptor function could be affected in prostate cells and by interaction with AP-1 and proteins, previous studies showed that c-jun alone inhibits the formation of androgen receptor-ARE complexes. Experiments described herein found that c-jun expression was increased by DHA treatment, and the transcriptional activity of androgen receptor decreased with increasing c-jun expression. The gene transfer experiments performed in this study further confirmed that the inhibition in androgen receptor function was due to of the increased levels of c-jun as a result of DHA.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an individual with prostate cancer or at risk of developing prostate cancer, comprising the steps of:

identifying an individual with prostate cancer or at risk of developing prostate cancer;

administering a dose of docosahexaenoic acid (DHA) and/or eicosapentaenoic acid (EPA) to said individual in an amount that is effective to inhibit the transactivating ability of an androgen receptor; and monitoring the transactivating ability of said androgen receptor in said individual, wherein inhibiting the transactivating ability of said androgen receptor inhibits the proliferation of prostate cancer cells, thereby treating said individual.

2. The method of claim 1, wherein said administration is selected from the group consisting of oral, transdermal, intravenous, intraperitoneal, and implanted.

3. The method of claim 1, wherein said effective dose is from about 5 mg/kg to about 25 mg/kg.

4. The method of claim 1, wherein said individual is a human.

5. A method of reducing the risk of recurrence of prostate cancer in an individual, wherein said individual previously had been treated for prostate cancer, comprising the step of:

administering a dose of docosahexaenoic acid (DHA) and/or eicosapentaenoic acid (EPA) to said individual in an amount that is effective to inhibit the transactivating ability of an androgen receptor, wherein inhibiting the transactivating ability of said androgen receptor inhibits the proliferation of prostate cancer cells, thereby reducing the risk of recurrence of prostate cancer in said individual.

6. The method of claim 5, further comprising the step of:

monitoring the transactivating ability of said androgen receptor in said individual.

7. The method of claim 5, wherein said previous treatment for prostate cancer in said individual comprised a radical prostectomy.

8. The method of claim 5, wherein said administration is selected from the group consisting of oral, transdermal, intravenous, intraperitoneal, and implanted.

9. The method of claim 5, wherein said effective dose is from about 5 mg/kg to about 25 mg/kg.

10. A method of treating an individual with prostate cancer or at risk of developing prostate cancer, comprising the steps of:
   identifying an individual with prostate cancer or at risk of developing prostate cancer; and
   administering a dose of docosahexaenoic acid (DHA) and/or eicosapentaenoic acid (EPA) to said individual in an amount that is effective to inhibit the transactivating ability of an androgen receptor, wherein said administration is selected from the group consisting of transdermal, intravenous, intraperitoneal, and implanted.

11. The method of claim 10, wherein said effective dose is from about 5 mg/kg to about 25 mg/kg.

12. A method of reducing the risk of recurrence of prostate cancer in an individual, wherein said individual previously had been treated for prostate cancer, comprising the step of:
   administering a dose of docosahexaenoic acid (DHA) and/or eicosapentaenoic acid (EPA) to said individual in an amount that is effective to inhibit the transactivating ability of an androgen receptor, wherein said administration is selected from the group consisting of transdermal, intravenous, intraperitoneal, and implanted.

13. The method of claim 12, wherein said effective dose is from about 5 mg/kg to about 25 mg/kg.

14. A method of treating an individual with prostate cancer or at risk of developing prostate cancer, comprising the steps of:
   identifying an individual with prostate cancer or at risk of developing prostate cancer;
   administering a dose of docosahexaenoic acid (DHA) and/or eicosapentaenoic acid (EPA) to said individual in an amount that is effective to inhibit the transactivating ability of an androgen receptor; and
   monitoring said individual for a dose-dependent reduction in prostate-specific antigen (PSA) levels,
   wherein said dose-dependent reduction in PSA correlates with a dose-dependent decrease in the transactivating ability of said androgen receptor.

15. The method of claim 14, further comprising:
   monitoring human glandular kallikrein (hK2) levels in said individual, wherein a reduction in hK2 correlates with a decrease in the transactivating ability of said androgen receptor.

16. The method of claim 14, further comprising:
   adjusting, if necessary, said dose of DHA and/or EPA to achieve or maintain said dose-dependent reduction in PSA.

17. A method of treating an individual with prostate cancer or at risk of developing prostate cancer, comprising the steps of:
   identifying an individual with prostate cancer or at risk of developing prostate cancer;
   administering a dose of docosahexaenoic acid (DHA) and/or eicosapentaenoic acid (EPA) to said individual in an amount that is effective to inhibit the transactivating ability of an androgen receptor; and
   monitoring human glandular kallikrein (hK2) levels in said individual, wherein a reduction in hK2 correlates with a decrease in the transactivating ability of said androgen receptor.

18. The method of claim 17, further comprising
   adjusting, if necessary, said dose of DHA and/or EPA to achieve or maintain said reduction in hK2.

19. A method of reducing the risk of recurrence of prostate cancer in an individual, wherein said individual previously had been treated for prostate cancer, comprising the step of:
   administering a dose of docosahexaenoic acid (DHA) and/or eicosapentaenoic acid (EPA) to said individual in an amount that is effective to inhibit the transactivating ability of an androgen receptor; and
   monitoring said individual for a dose-dependent reduction in prostate-specific antigen (PSA) levels,
   wherein said dose-dependent reduction in PSA correlates with a dose-dependent decrease in the transactivating ability of said androgen receptor.

20. The method of claim 19, further comprising:
   monitoring human glandular kallikrein (hK2) levels in said individual, wherein a reduction in hK2 correlates with a decrease in the transactivating ability of said androgen receptor.

21. The method of claim 19, further comprising:
   adjusting, if necessary, said dose of DHA and/or EPA to achieve or maintain said dose-dependent reduction in PSA.

22. A method of reducing the risk of recurrence of prostate cancer in an individual, wherein said individual previously had been treated for prostate cancer, comprising the step of:
   administering a dose of docosahexaenoic acid (DHA) and/or eicosapentaenoic acid (EPA) to said individual in an amount that is effective to inhibit the transactivating ability of an androgen receptor; and
   monitoring human glandular kallikrein (hK2) levels in said individual,
   wherein a reduction in hK2 correlates with a decrease in the transactivating ability of said androgen receptor.

23. The method of claim 22, further comprising:
   adjusting, if necessary, said dose of DHA and/or EPA to achieve or maintain said reduction in hK2.

* * * * *